United States Patent

Bauer et al.

Patent Number: 5,527,944
Date of Patent: Jun. 18, 1996

[54] β-HYDROXYOXIME ETHERS AND SOLUTIONS OR DISPERSIONS CROSSLINKABLE AT ROOM TEMPERATURE WITH β-HYDROXYOXIME ETHERS

[75] Inventors: Gerhard Bauer, Weinheim; Oral Aydin, Mannheim; Beate Strecker, Ludwigshafen; Alfred Oftring, Bad Durkheim, all of Germany

[73] Assignee: BASF Aktiengesellschaft, Ludwigshafen, Germany

[21] Appl. No.: 530,011

[22] Filed: Sep. 19, 1995

Related U.S. Application Data

[63] Continuation of Ser. No. 202,461, Feb. 28, 1994, abandoned.

[30] Foreign Application Priority Data

Mar. 2, 1993 [DE] Germany ............ 43 06 392.6

[51] Int. Cl.[6] .................................. C07C 291/00
[52] U.S. Cl. ........................... 558/299; 525/374
[58] Field of Search .............................. 558/299

[56] References Cited

U.S. PATENT DOCUMENTS 4,396,738  8/1983  Powell et al. .

FOREIGN PATENT DOCUMENTS

| | | |
|---|---|---|
| 0369944 | 5/1990 | European Pat. Off. . |
| 05160074 | 12/1992 | European Pat. Off. . |
| 0516074 | 12/1992 | European Pat. Off. . |
| 2658938 | 7/1978 | Germany . |
| 3112117 | 10/1982 | Germany . |
| 3521618 | 12/1986 | Germany . |
| 3807555 | 9/1988 | Germany . |
| 93/01395 | 1/1993 | WIPO . |

OTHER PUBLICATIONS

Chemical Abstracts CA113(25):230781m, Stanek et al. E.P. 369,944, 1990.

*Primary Examiner*—Bernard Lipman
*Attorney, Agent, or Firm*—Oblon, Spivak, McClelland, Maier & Neustadt

[57] ABSTRACT

A compound of the formula

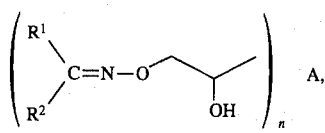

where $R^1$ and $R^2$, independently of one another, are each $C_1$–$C_{10}$-alkyl, $C_1$–$C_{10}$-alkoxy, $C_5$–$C_{10}$-cycloalkyl or $C_5$–$C_{10}$-aryl, each of which may furthermore contain from 1 to 3 non-adjacent nitrogen, oxygen or sulfur atoms as hetero atoms in the carbon chain or carbon ring and may be substituted by 1 to 3 $C_1$–$C_4$-alkyl or $C_1$–$C_4$-alkoxy groups, $R^1$ or $R^2$ may be hydrogen or $R^1$ and $R^2$ together form a bridge of 2 to 14 carbon atoms, where some of the carbon atoms may furthermore be part of an aromatic ring system, A is an n-valent organic radical and n is an integer equal to or greater than 2.

3 Claims, No Drawings

β-HYDROXYOXIME ETHERS AND SOLUTIONS OR DISPERSIONS CROSSLINKABLE AT ROOM TEMPERATURE WITH β-HYDROXYOXIME ETHERS

This application is a continuation of application Ser. No. 08/202,461, filed on Feb. 28, 1994, now abandoned.

The present invention relates to a compound of the formula

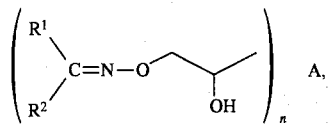 I where $R^1$ and $R^2$, independently of one another, are each $C_1$–$C_{10}$-alkyl, $C_1$–$C_{10}$-alkoxy, $C_5$–$C_{10}$-cycloalkyl or $C_5$–$C_{10}$-aryl, each of which may furthermore contain from 1 to 3 non-adjacent nitrogen, oxygen or sulfur atoms as hetero atoms in the carbon chain or carbon ring and may be substituted by 1 to 3 $C_1$–$C_4$-alkyl or $C_1$–$C_4$-alkoxy groups, $R^1$ or $R^2$ may be hydrogen or $R^1$ and $R^2$ together form a bridge of 2 to 14 carbon atoms, where some of the carbon atoms may furthermore be part of an aromatic ring system, A is an n-valent organic radical and n is an integer equal to or greater than 2.

The present invention furthermore relates to dispersions or solutions of free radical polymers, polycondensates or polyadducts which contain compounds of the formula I.

Copolymers which are used in coating materials or adhesives are often crosslinkable copolymers. As a result of crosslinking, it is possible to obtain, for example, protective coatings, lacquers or adhesive coatings having good elastic properties, high cohesion, i.e. internal strength, and high resistance to chemicals and to solvents.

For crosslinking, a crosslinking agent which reacts with functional groups in the copolymer is generally added to the copolymers.

Examples of possible crosslinking agents are polyisocyanates, which react with hydroxyl or amino groups.

DE-A-35 21 618 discloses corresponding aqueous adhesive formulations in which polyisocyanates dispersed in water are added as crosslinking agents to copolymers obtained by free radical polymerization. Similar adhesive formulations are also described in U.S. Pat. No. 4,396,738 and DE-A-31 12 117.

However, the disadvantage of the aqueous formulations is the poor shelf life. Dispersing of the polyisocyanate in water and mixing with the copolymer therefore must not be carried out until shortly before said polyisocyanate is used as the crosslinking agent.

A longer shelf life can be achieved by reacting the isocyanate groups with blocking agents, for example oximes, caprolactam, phenols or dialkyl maleates. The blocked polyisocyanates obtained are hydrolyzed in aqueous dispersion only to a minor extent.

DE-A-38 07 555 relates to such an oxime-blocked diisocyanate which is dispersed in water and is suitable as an additive for polymers dispersed in water.

However, crosslinking reactions occur only after elimination of the blocking agent at above about 130° C.

Conventional aqueous adhesive formulations having polyisocyanates as a crosslinking agent therefore are either unstable during storage and are hence used only as a 2-component system or do not undergo crosslinking until higher temperatures.

Aqueous dispersions which have a long shelf life and crosslink at room temperature after removal of the solvent are disclosed in EP-A-3516. These dispersions contain polyhydrazides which react with monomers having carbonyl groups and present as polymerized units in the copolymer.

The non-prior published German Patent Application P 42 19 384.2 discloses oxime ethers as crosslinking agents. EP-A-516 074 describes aminooxy derivatives as crosslinking agents for copolymers containing keto or aldehyde groups.

There is in principle a need for further dispersions which crosslink at room temperature, in order to be able to provide alternatives to polyhydrazide crosslinking. Furthermore, these dispersions should have good performance characteristics, for example good adhesion, in particular good wet adhesion to various substrates.

It is an object of the present invention to provide dispersions or solutions of crosslinkable copolymers, which dispersions or solutions have a long shelf life, contain a crosslinking agent and are crosslinkable at room temperature.

We have found that this object is achieved by the compound defined above and by dispersions or solutions which contain this compound.

The compound of the formula I is suitable as a crosslinking agent or adhesion promoter in dispersions or solutions of free radical polymers, polycondensates or polyadducts.

Crosslinking of the free radical polymers, polycondensates or polyadducts containing keto or aldehyde groups with crosslinking agents of the formula I occurs on removal of the liquid phase of the dispersion or solution.

Crosslinking groups are the β-hydroxyoxime ether groups

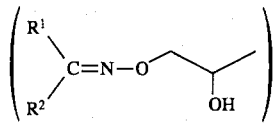

which react with, for example, keto or aldehyde groups.

The dispersion or solution to which compounds I are added as crosslinking agents therefore preferably contains a polymer, polycondensate or polyadduct which comprises from 0.001 to 20, preferably from 0.01 to 10, very particularly preferably from 0.05 to 3, % by weight of aldehyde groups —CHO— or keto groups —CO—.

It may be, for example, a copolymer obtained by free radical polymerization, a polyester in the form of a polycondensate or a polyurethane in the form of a polyadduct.

In the case of the copolymers obtained by free radical polymerization, the aldehyde or keto groups are preferably incorporated as polymerized units by means of ethylenically unsaturated compounds which contain these groups.

They are preferably ethylenically unsaturated compounds having one or two aldehyde or keto groups or one aldehyde and one keto group and an olefinic double bond capable of free radical polymerization (referred to below as monomers a)).

In the case of a polyester, the relevant compounds may be, for example, monoalcohols, diols, monocarboxylic acids or dicarboxylic acids, and in the case of a polyurethane they may be, for example, mono- or diisocyanates or monoalcohols or diols, each of which contain aldehyde or keto groups.

Examples of monoalcohols are hydroxyacetone, hydroxybenzaldehyde, acetoin and benzoin.

Suitable monocarboxylic acids are, for example, ketocarboxylic acids, such as pyruvic acid or levulinic acid.

Furthermore, compounds having aldehyde or keto groups not only can be bound in the polymers, polycondensates or polyadducts as part of the main chain but also can be bound to the polymers, polycondensates or polyadducts by reaction with reactive groups in the polymer main chain.

A copolymer which is obtained by free radical polymerization and consists of the monomers a) which contain aldehyde or keto groups and furthermore monomers b) and c) is preferred.

Examples of suitable monomers a) are acrolein, methacrolein, vinyl alkyl ketones where the alkyl radical is of 1 to 20, preferably 1 to 10, carbon atoms, formylstyrene, alkyl (meth)acrylates having one or two keto or aldehyde or one aldehyde and one keto group in the alkyl radical, the latter preferably having a total of 3 to 10 carbon atoms, for example (meth)acryloyloxyalkylpropanals, as described in DE-A-27 22 097. N-Oxoalkyl(meth)acrylamides, as described, for example, in U.S. Pat. No. 4,226,007, De-A-20 61 213 or DE-A-22 07 209, are also suitable.

Acetoacetyl (meth)acrylate, acetoacetoxyethyl (meth)acrylate and especially diacetoacrylamide are particularly preferred.

The copolymer contains in particular from 20 to 99.99, preferably from 60 to 99.9, particularly preferably from 80 to 99.5, % by weight, based on the copolymer, of the main monomers b).

Suitable monomers b) are esters of acrylic or methacrylic acid with alkyl alcohols of 1 to 20 carbon atoms. Examples of such alcohols are methanol, ethanol, n-propanol, isopropanol, n-butanol, sec-butanol, tertbutanol, n-pentanol, isoamyl alcohol, n-hexanol, octanol, 2-ethylhexanol, lauryl alcohol and stearyl alcohol.

Good results are obtained with alkyl (meth)acrylates having a $C_1$–$C_{10}$-alkyl radical, such as methyl methacrylate, methyl acrylate, n-butyl acrylate, ethyl acrylate and 2-ethylhexyl acrylate.

Mixtures of the alkyl (meth)acrylates are also particularly suitable.

Vinyl esters of carboxylic acids of 1 to 20 carbon atoms, such as vinyl laurate, vinyl stearate, vinyl propionate and vinyl acetate, are also suitable.

Suitable vinylaromatic compounds of up to 20 carbon atoms are vinyltoluene, α- and p-styrene, α-butylstyrene, 4-n-butylstyrene, 4-n-decylstyrene and preferably styrene. Examples of ethylenically unsaturated nitriles are acrylonitrile and methacrylonitrile.

The vinyl halides are chlorine-, fluorine- or bromine-substituted ethylenically unsaturated compounds, preferably vinyl chloride or vinylidene chloride.

Examples of nonaromatic hydrocarbons of 2 to 8 carbon atoms having at least two conjugated olefinic double bonds are butadiene, isoprene and chloroprene.

The monomers b) can in particular also be used as a mixture, especially to obtain desired glass transition temperatures of the copolymer.

Examples of further suitable copolymerizable monomers c), i.e. those not included under a) and b), are esters of acrylic and methacrylic acid with alcohols of 1 to 20 carbon atoms which, apart from the oxygen atom in the alcohol group, contain at least one further hetero atom and/or which contain an aliphatic or aromatic ring.

Examples are 2-ethoxyethyl acrylate, 2-butoxyethyl (meth)acrylate, dimethylaminoethyl (meth)acrylate, diethylaminoethyl (meth)acrylate, aryl, alkaryl or cycloalkyl (meth)acrylate, such as cyclohexyl (meth)acrylate, phenylethyl (meth)acrylate or phenylpropyl (meth)acrylate, or acrylates or heterocyclic alcohols, such as furfuryl (meth)acrylate.

Further comonomers, such as (meth)acrylamide and its derivates substituted by $C_1$–$C_4$-alkyl at the nitrogen, may also be mentioned.

Comonomers having hydroxyl functional groups, for example $C_1$–$C_{15}$-alkyl (meth)acrylates which are substituted by one or two hydroxyl groups, are particularly important. Of particular importance as comonomers having hydroxyl functional groups are $C_1$–$C_8$-hydroxyalkyl (meth)acrylates, such as n-hydroxyethyl, n-hydroxypropyl or n-hydroxybutyl (meth)acrylate.

The presence of comonomers having salt-forming groups is advisable, for example, for the preparation of self-dispersible copolymers which are suitable, for example, for aqueous secondary dispersions. Comonomers having salt-forming groups are in particular itaconic acid, acrylic acid and methacrylic acid.

The amount by weight of the further comonomers in the copolymer may be in particular from 0 to 50, preferably from 0 to 20, very particularly preferably from 0 to 10, % by weight.

The amounts of the monomers a), b) and c) sum to 100% by weight.

The amount of the monomers a) is chosen so that the abovementioned content of aldehyde or keto groups is obtained in the copolymer.

The copolymer is prepared in general by free radical polymerization. Suitable polymerization methods, such as mass, solution, suspension or emulsion polymerization, are known to the skilled worker.

The copolymer is preferably prepared by solution polymerization with subsequent dispersing in water or particularly preferably by emulsion polymerization, the copolymer being obtained as an aqueous dispersion.

In the emulsion polymerization, the comonomers can be polymerized in the conventional manner in the presence of a water-soluble initiator and of an emulsifier at, preferably, from 30° to 95° C.

Suitable initiators are, for example, sodium persulfate, potassium persulfate, ammonium persulfate, tert-butyl hydroperoxides, water-soluble azo compounds and redox initiators.

Examples of emulsifiers used are alkali metal salts of relatively long-chain fatty acids, alkylsulfates, alkylsulfonates, alkylated arylsulfonates and alkylated diphenyl ether sulfonates.

Other suitable emulsifiers are reaction products of alkylene oxides, in particular ethylene oxide or propylene oxide, with fatty alcohols, fatty acids or phenol, and alkylphenols.

In the case of aqueous secondary dispersions, the copolymer is first prepared by solution polymerization in an organic solvent and then dispersed in water with the addition of salt formers, for example of ammonia to carboxyl-containing copolymers, without the use of an emulsifier or dispersant. The organic solvent can be distilled off. The preparation of aqueous secondary dispersions is known to the skilled worker and is described, for example, in DE-A-37 20 860.

Regulators may be used in the polymerization in order to adjust the molecular weight. For example, SH-containing compounds, such as mercaptoethanol, mercaptopropanol, thiophenol, thioglycerol, ethyl thioglycolate, methyl thioglycolate and tert-dodecyl mercaptan, are suitable.

The type and amount of the comonomers is expediently chosen so that the copolymer obtained has a glass transition temperature of, preferably, from −60° to +140° C. Depending on whether rigid or flexible coatings are desired, high or low glass transition temperatures are obtained through the choice of the monomers. The glass transition temperature of the copolymer can be determined by conventional methods, such as differential thermal analysis or differential scanning calorimetry (cf. for example ASTM 3418/82, midpoint temperature).

The dispersion or solution contains a compound of the formula I as an adhesion promoter or as a crosslinking agent.

In the formula I, $R^1$ and $R^2$, independently of one another, may each be $C_1$–$C_{10}$-alkyl, $C_1$–$C_{10}$-alkoxy, $C_5$–$C_{10}$-cycloalkyl or $C_5$–$C_{10}$-aryl, each of which may furthermore contain 1 to 3 nonadjacent nitrogen, oxygen or sulfur atoms in the carbon chain or in the carbon ring and may be substituted by 1 to 3 $C_1$–$C_4$-alkyl or $C_1$–$C_4$-alkoxy groups, and $R^1$ or $R^2$ may each furthermore be hydrogen, or $R^1$ and $R^2$ together form a bridge of 2 to 14 carbon atoms, where some of the carbon atoms may also be part of an aromatic ring system.

$R^1$ and $R^2$ are each preferably hydrogen, $C_1$–$C_6$-alkyl or $C_1$–$C_6$-alkoxy. In the case of hydrogen, only one of the radicals $R^1$ or $R^2$ may be hydrogen.

Suitable organic radicals A are, for example, unsaturated or, preferably, saturated linear, branched or cyclic hydrocarbon radicals which may be interrupted by nonadjacent nitrogen, sulfur or, in particular, oxygen atoms. $C_2$–$C_8$-Alkylene or groups of the formula —O—$(CH_2)_x$—O—, where x is from 2 to 20, are particularly preferred.

Other suitable radicals A are aromatic hydrocarbon radicals or hydrocarbon radicals which contain both aliphatic and aromatic hydrocarbon groups.

Examples of the latter are in particular $C_5$–$C_{12}$-arylene radicals or radicals of the formula

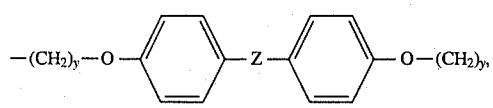

where Z is a linear or branched aliphatic hydrocarbon radical of 1 to 5 carbon atoms and y is an integer of from 1 to 3.

However, A may also be, for example, a polymeric radical as obtainable, for example, by polycondensation of bisphenol A with epichlorohydrin.

n is an integer equal to or greater than 2, preferably from 2 to 30, particularly preferably from 2 to 4, very particularly preferably 2.

Low molecular weight compounds are generally adequate for use as a crosslinking agent or adhesion promoter, and it is therefore unnecessary to use higher molecular weight compounds. The molecular weight of the compounds I is therefore in general less than 5,000, preferably less than 1,000, g/mol.

The amount by weight of the compound of the formula I in the dispersions or solutions is preferably from 0.01 to 30, particularly preferably from 0.1 to 20, very particularly preferably from 0.1 to 5, % by weight, based on the polymer, polycondensate or polyadduct. Advantageously, the content in the case of keto- or aldehyde-containing free radical polymers, polycondensates or polyadducts is chosen so that the ratio of the β-hydroxyoxime ether groups to the keto and/or aldehyde groups is roughly equimolar.

In the dispersions or solutions, the compounds may undergo partial hydrolysis, for example in the presence of acids, so that β-hydroxyaminooxy compounds or groups may be formed even in small amounts. These β-hydroxyaminooxy groups can likewise undergo crosslinking with keto or aldehyde groups and also help to improve adhesion.

Metal salts or metal complexes which are present in the dispersions or solutions or are added thereto generally do not adversely affect the crosslinking or improvement in adhesion to compounds I.

The compounds of the formula I can be prepared in a simple manner by reacting epoxy compounds with oximes. Examples of suitable epoxy compounds are alkanediol diglycidyl ethers of the formula

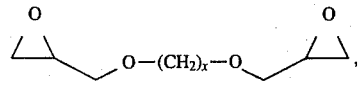

epoxidized α-olefins of the formula

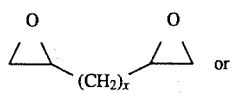

bisphenol diglycidyl ethers of the formula

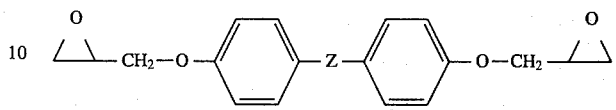

in particular bisphenol A diglycidyl ether, where Z has the abovementioned meanings.

Examples of suitable oximes are those of aliphatic, cycloaliphatic or aromatic aldehydes or ketones, for example acetone oxime, methyl ethyl ketoxime, diethyl ketoxime, methyl isopropyl ketoxime, methyl isobutyl ketoxime, diisopropyl ketoxime, cyclohexanone oxime, 2-methylcyclohexanone oxime, 2,6-dimethylcyclohexanone oxime, acetophenone oxime, benzophenone oxime or diethyl glyoxime. Oximes of aliphatic ketones or aldehydes having a keto or aldehyde group and a total of 3 to 12 carbon atoms, in particular acetone oxime and methyl ethyl ketoxime, are preferred.

The compounds I can be prepared in a simple manner by reacting the oxime in a first step with a base, e.g. NaOH, or another nucleophile. This is likely to give an anion having a negative charge on the oxygen atom adjacent to the oxime nitrogen. The reaction product can then be reacted with the epoxy compound, for example at from 0° to 100° C. in particular from 50° to 80° C., to give the compound I.

The solids content of the novel dispersion or solution is preferably from 20 to 90, in particular from 30 to 70, % by weight.

The novel dispersions or solutions are suitable as coating materials for various substrates having plastic, wood or metal surfaces or, for example, for textiles, fleeces, leather or paper. They are also suitable for applications in construction chemistry, for example as adhesives, sealing compounds, binders or the like. The coatings may be, for example, surface coatings with or without pigments, also for decorative purposes, protective coatings or adhesive coatings.

An aqueous dispersion of a copolymer obtained by free radical polymerization, in particular of a copolymer containing keto and/or aldehyde groups, is particularly suitable for the stated uses.

The aqueous dispersion may also contain organic, preferably water-miscible solvents as auxiliary solvents.

The novel dispersion or solution may contain conventional assistants and additives, depending on the intended use. These include, for example, fillers, such as quartz powder, quartz sand, finely divided silica, barite, calcium carbonate, chalk, dolomite or talc, which are often used together with suitable wetting agents, for example polyphosphates, such as sodium hexametaphosphate, naphthalenesulfonic acid, or ammonium or sodium polyacrylates, the wetting agents generally being added in amounts of from 0.2 to 0.6% by weight, based on the filler.

For use as a lacquer or varnish, the dispersion or solution may also contain film forming assistants, pigments, flatting agents, thickeners, pigment dispersants, antifoams, etc. and also other natural or synthetic resins, e.g. alkyd resins, polyurethane resins, etc.

Fungicides for preservation are, if desired, used in general in amounts of from 0.02 to 1% by weight, based on the total dispersion or solution. Suitable fungicides are, for example, phenol or cresol derivatives or organotin compounds.

The novel dispersions or solutions, in particular in the form of an aqueous dispersion of a free radical copolymer, are particularly suitable as a sealing compound or adhesive, in particular, for example, as a laminated adhesive for the production of laminated films and high-gloss films. As adhesives, the dispersions may contain not only the above-mentioned additives but also special assistants and additives conventionally used in adhesives technology. These include, for example, thickeners, plasticizers or tackifiers, for example natural resins or modified resins, such as rosin esters, or synthetic resins, such as phthalate resins.

Dispersions which are used as adhesives particularly preferably contain alkyl (meth)acrylates as comonomers b) in the copolymer.

The glass transition temperature of the copolymers is preferably brought to values of from 0° to –40° C. when said copolymers are used as adhesive formulations.

When used as adhesives, the dispersions surprisingly also exhibit very good adhesion, in particular wet adhesion.

The pH of the dispersion is preferably brought to 2–9, since the crosslinking reaction with the copolymers can be acid-catalyzed.

The novel dispersions or solutions which contain compounds of the formula I have a long shelf life. The crosslinking reaction, for example the keto and/or aldehyde groups, occurs at as low as room temperature on removal of the liquid phase, for example on volatilization of the water.

The volatilization of the water can be accelerated by increasing the temperature, for example to 30°–100° C.

In the coating of substrates, it is in principle also possible to apply a dispersion or solution of the polymer, polycondensate or polyadduct, which solution or dispersion does not contain the hydroxylamines or oxime ether derivatives, to a surface to which compounds of the formula I have been applied beforehand in a separate operation.

In this case, the compounds act as primers.

After application of the dispersion or solution, the crosslinking then begins or an improvement in adhesion is observed.

EXAMPLES

Preparation of the copolymers Copolymer dispersion 1

200 g of demineralized water, 37 g of feed 1 (see below) and 20 g of feed 2 were initially taken in a reaction vessel having a stirrer and two feed vessels (feed 1 and feed 2) and were heated to 85° C. After 15 minutes, feed 1 was added uniformly in the course of 2 hours and feed 2 uniformly in the course of 2.5 hours. After the final addition of initiator (feed 2), the dispersion was stirred for a further hour at 85° C.

Feed 1: (This feed was stirred during the polymerization)
107.5 g of demineralized water
400 g of ethyl acrylate
90 g of methyl methacrylate
50 g of 20% strength by weight aqueous diacetoneacrylamide solution
50 g of 20% strength by weight solution of the sodium salt of p-dodecyldiphenyl ether disulfonate in water (emulsifier)
50 g of 20% strength by weight solution of the reaction product of p-isononylphenol with 50 mol of ethylene oxide in water (emulsifier) Feed 2:
100 g of demineralized water
3 g of sodium persulfate Copolymer dispersions 2 and 3 were prepared in a similar manner (Table 1).

TABLE 1

| | Composition of the copolymers in % by weight | | | |
|---|---|---|---|---|
| Copolymer dispersion | EA | MMA | DAA | AAEM |
| 1 | 80 | 18 | 2 | |
| 2 | 96 | | 4 | |
| 3 | 77.7 | 17.4 | | 4.9 |

Abbreviations
EA: Ethyl acrylate
MMA: Methyl methacrylate
DAA: Diacetoneacrylamide
AAEM: Acetoacetoxyethyl methacrylate Preparation of the crosslinking agent Crosslinking agent A

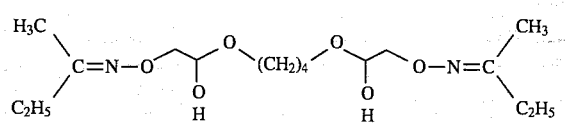

100 g (1.15 mol) of butanone oxime in 100 ml of toluene were initially taken. 40 g (0.50 mol) of 50% strength by weight NaOH were then added dropwise at room temperature in the course of about 20 minutes. During this procedure, the temperature increased to about 35° C. The reaction mixture was refluxed at 120° C. and a total of 24.3 g of water was distilled off.

The reaction solution obtained was cooled to 50° C. under nitrogen, and 225.1 g (0.57 mol) of butanediol diglycidyl ether were added dropwise in the course of 6 hours. The mixture was kept at 50° C. for a further hour, after which no unconverted oxide was detectable. The organic solution was extracted twice with water. Residual toluene was distilled off from the combined aqueous phases. Finally, 336 g of an orange aqueous solution of crosslinking agent A, having a solids content of 24.1% by weight, were obtained.

Crosslinking agent B

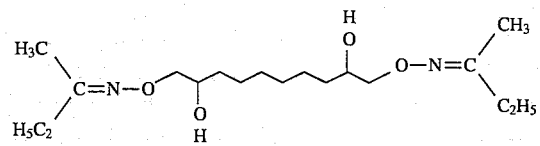

The procedure was as described for crosslinking agent A. Instead of butanediol diglycidyl ether, however, α,ω-diepoxydecane was added. After unconverted oxide was no longer detectable, the toluene was removed at from 70° to 80° C. under reduced pressure (<10 mbar). Crosslinking agent B was obtained as a reddish brown, viscous liquid.
Test for crosslinkablility (swelling) and testing of performance characteristics (high-gloss film test and laminated film test)

For the tests, crosslinking agents A and B were added to the dispersions 1 to 3 in each case in equimolar amounts, based on the keto or aldehyde groups.
Swelling The dispersion formulations were converted into films and the latter were dried for 1 week at room temperature. Thereafter, the swelling behavior was investigated as a measure of the degree of crosslinking of these films in tetrahydrofuran by storing about 1 g of the film samples in tetrahydrofuran for 1 day and measuring the solvent absorption in %.

Increasing crosslinking density is accompanied by a decrease in the solvent absorption during swelling.

Polymers which exhibit little or no crosslinking are dissolved or swell to an excessive extent owing to the extremely low crosslinking density.

The results are shown in Table 2.

High-gloss film test

The dispersion formulations were applied by knife coating to give a dry layer having a thickness of 5 g/m² on cardboard cartons printed with offset inks and were dried at 60° C. and, after about 30 seconds, laminated by biaxially oriented polypropylene films (o-PP).

A test was carried out to determine whether paper and ink are torn off from the cardboard box when the film is pulled off (peel test) (rating 1: paper or ink completely torn off, rating 2: paper or ink partially torn off) and whether the film becomes detached or does not adhere firmly in the region of grooves (indentations in the cardboard box) (groove stability:+=no detachment at the groove, −=detachment at the groove and +/−=partial detachment at the groove).

The results are shown in Table 2.

Laminated film test

The dispersion formulations were applied by knife coating to give a dry layer having a thickness of 3 g/m² on a polyethylene terephthalate film (PETP) heated to 50° C. and, after 20 seconds, were laminated with a polyethylene film of PE (corona-preheated). The films were then stored for 7 days at room temperature and under standard humidity conditions and then cut into 2 cm wide strips. These strips were then peeled off at 23° C. at an angle of 180° C. and at a speed of 100 m/min. The peeling force in N for the 2 cm wide strips was determined (Table 2).

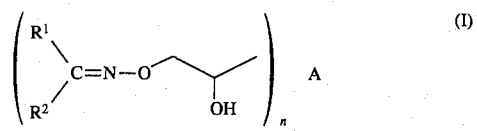

where $R^1$ and $R^2$, independently of one another, are each $C_1$–$C_{10}$-alkyl, $C_1$–$C_{10}$-alkoxy, $C_5$–$C_{10}$-cycloalkyl or $C_5$–$C_{10}$-aryl, each of which may furthermore contain from 1 to 3 non-adjacent nitrogen, oxygen or sulfur atoms as heteroatoms in the carbon chain or carbon ring and may be substituted by 1 to 3 $C_1$–$C_4$-alkyl or $C_1$–$C_4$-alkoxy groups, $R^1$ or $R^2$ may be hydrogen or $R^1$ and $R^2$ together form a bridge of 2 to 14 carbon atoms, where some of the carbon atoms may furthermore be part of an aromatic ring system, A is an n-valent organic radical selected from the group consisting of $C_2$–$C_8$ alkylene; —$O(CH_2O_xO$— where x is from 2 to 20; $C_5$–$C_{12}$ arylene;

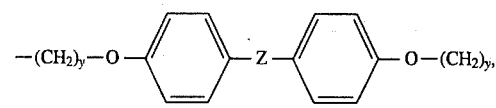

where Z is a linear or branched aliphatic hydrocarbon radical of 1 to 5 carbon atoms and y is an integer of from 1 to 3; and a radical obtained by polycondensation of bisphenol A with epichlorohydrin; and n is an integer equal to or greater than 2.

2. The compound of claim 1 wherein $R^1$ is methyl, $R^2$ is ethyl, A is —O—$(CH_2)_4$—O— and n is 2.

3. The compound of claim 1 wherein $R^1$ is methyl, $R^2$ is ethyl, A is —$(CH_2)_6$— and n is 2.

TABLE 2

| | | Test results | | | |
|---|---|---|---|---|---|
| | | Swelling | Lamination of high-gloss films | | Film lamination |
| Dispersion | Crosslinking agent | Solvent absorption % by weight | Peel test | Groove stability | Peel test |
| 1 | — | —* | 2 | — | 0.5 |
| 2 | — | —* | 2 | — | 0.5 |
| 3 | — | —* | 2 | — | 0.5 |
| 1 | A | 1940 | 1 | + | 1.9 |
| 2 | A | 1800 | 1 | + | 2.2 |
| 3 | A | 2000 | 1 | + | 2.0 |
| 1 | B | 2100 | 1 | + | 1.5 |
| 2 | B | 1920 | 1 | + | 1.9 |
| 3 | B | 2060 | 1 | + | 1.6 |

*Film is dissolved

We claim:

1. A compound of the formula